United States Patent
Koob et al.

(10) Patent No.: US 10,960,027 B2
(45) Date of Patent: Mar. 30, 2021

(54) COMPOSITIONS AND METHODS OF TREATMENT WITH AMNIOTIC FLUID

(71) Applicant: MiMedx Group, Inc., Marietta, GA (US)

(72) Inventors: Thomas J. Koob, Marietta, GA (US); Michelle Massee, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 148 days.

(21) Appl. No.: 16/087,358

(22) PCT Filed: Mar. 23, 2017

(86) PCT No.: PCT/US2017/023893
§ 371 (c)(1),
(2) Date: Sep. 21, 2018

(87) PCT Pub. No.: WO2017/165698
PCT Pub. Date: Sep. 28, 2017

(65) Prior Publication Data
US 2020/0129562 A1    Apr. 30, 2020

Related U.S. Application Data

(60) Provisional application No. 62/312,403, filed on Mar. 23, 2016, provisional application No. 62/312,379, filed on Mar. 23, 2016, provisional application No. 62/312,391, filed on Mar. 23, 2016.

(51) Int. Cl.

| | |
|---|---|
| *A61K 35/50* | (2015.01) |
| *A61K 9/00* | (2006.01) |
| *A61K 9/06* | (2006.01) |
| *A61K 9/19* | (2006.01) |
| *A61K 47/34* | (2017.01) |
| *A61K 47/36* | (2006.01) |
| *A61K 47/42* | (2017.01) |
| *A61K 47/46* | (2006.01) |
| *A61M 5/31* | (2006.01) |
| *A61M 11/00* | (2006.01) |

(52) U.S. Cl.
CPC ............ *A61K 35/50* (2013.01); *A61K 9/0014* (2013.01); *A61K 9/0019* (2013.01); *A61K 9/0078* (2013.01); *A61K 9/06* (2013.01); *A61K 9/19* (2013.01); *A61K 47/34* (2013.01); *A61K 47/36* (2013.01); *A61K 47/42* (2013.01); *A61K 47/46* (2013.01); *A61M 5/31* (2013.01); *A61M 11/00* (2013.01)

(58) Field of Classification Search
None
See application file for complete search history.

(56) References Cited

U.S. PATENT DOCUMENTS

| | | | | |
|---|---|---|---|---|
| 1,696,958 | A | * | 1/1929 | Johnson ................. A61K 35/50 424/528 |
| 2014/0336600 | A1 | | 11/2014 | Harrell |
| 2015/0024483 | A1 | | 1/2015 | Riordan et al. |
| 2016/0000968 | A1 | | 1/2016 | Koob et al. |
| 2016/0067287 | A1 | | 3/2016 | McQueen et al. |
| 2016/0256500 | A1 | | 9/2016 | White |
| 2017/0042943 | A1 | | 2/2017 | Namin et al. |
| 2020/0077987 | A1 | * | 3/2020 | Harrell ................. A61B 8/0841 |

FOREIGN PATENT DOCUMENTS

| | | |
|---|---|---|
| WO | WO 2006/091546 A2 | 8/2006 |
| WO | WO 2015/134946 A1 | 9/2015 |
| WO | WO 2015/171142 A1 | 11/2015 |

OTHER PUBLICATIONS

Cho, C. et al. Proteomics Anaylsis of Human Amniotic Fluid. Molecular & Cellular Proteomics, 1406-1415, May 2007. (Year: 2007).*
Extended European Search Report for European Patent Application No. 17771189.2, dated Dec. 12, 2019.
Kara et al., "Effectiveness of Human Amniotic Fluid and Amniotic Membrane in Preventing Spinal Epidural Fibrosis in an Experimental Rat Model," J. Neurol. Sci., 32(2):293-302, (2015).
International Search Report and Written Opinion of the International Searching Authority for PCT International Application No. PCT/US2017/23893 dated Jun. 19, 2017.

* cited by examiner

*Primary Examiner* — Ralph J Gitomer
(74) *Attorney, Agent, or Firm* — Alston & Bird LLP

(57) ABSTRACT

The present disclosure provides compositions composed of amniotic fluid and/or modified amniotic fluid, a pharmaceutically acceptable carrier, and optionally a placental tissue graft, micronized placental tissue components, or extracts derived therefrom. Also described are systems and apparatuses for administering or storing said compositions, as well as methods of treatment using said compositions.

19 Claims, 5 Drawing Sheets

COMPOSITIONS AND METHODS OF TREATMENT WITH AMNIOTIC FLUID

CROSS REFERENCE TO RELATED APPLICATIONS

This application is a U.S. National Stage entry of International Application No. PCT/US2017/023893 filed Mar. 23, 2017, which claims priority of U.S. Provisional Application No. 62/312,379, filed Mar. 23, 2016, U.S. Provisional Application No. 62/312,403, filed Mar. 23, 2016, and U.S. Provisional Application No. 62/312,391, filed Mar. 23, 2016, each of which are incorporated by reference in their entirety for all purposes.

FIELD OF THE INVENTION

This disclosure relates generally to compositions of amniotic fluid, which may be modified or unmodified. This disclosure also relates to the treatment of certain diseases and/or disorders, such as skin diseases or disorders, or pulmonary diseases or disorders, with said compositions. This disclosure also relates to systems for administering said compositions.

BACKGROUND

During pregnancy amniotic fluid fills the amniotic sac, sustains fetal growth, and provides mechanical cushioning to the fetus. This complex, dynamic fluid contains nutrients, growth factors, and cells which circulate as the fetus swallows and "inhales" the fluid and then releases it back into the amniotic sac. While in utero, the amniotic fluid helps the developing fetus move within the womb, promotes proper lung development, and regulates the temperature around the fetus, among other functions.

Amniotic fluid has been used for decades for diagnostic purposes, for example, prenatal genetic screening, determining fetal lung maturity, metabolic diseases, fetal infections and intrauterine infections. Removing a sample of fluid through amniocentesis can provide information about the sex, health and development of the fetus. In addition, abnormal amounts of amniotic fluid, including too much ("polyhydramnios") or too little ("oligohydramnios"), may be a sign of a pregnancy complication.

Human skin is prone to developing various sores or becoming otherwise traumatized due to injury, disease, exposure to toxins or caustic substances. Skin diseases are not only unsightly but also can be very painful. Wounds or sores covering relatively large surface areas of the skin are often difficult to treat and may heal slowly. Some sores may not heal on their own. If left untreated, a skin sore or wound may become infected. Some of the most common skin diseases and disorders include eczema, irritation reaction (such as that caused by poison ivy, poison oak or poison sumac), laser skin ablation, dermatitis, wounds and skin traumas. For centuries, people have been using various substances, both naturally occurring and synthetic, in an effort to promote healing of skin tissues. Often, it is desirable that these substances be applied directly to the area of the wound or sore in the form of a lotion or ointment. Continued improvement in the treatment of skin diseases and conditions would be a benefit to those suffering from these types of conditions.

Diseases and disorders of the pulmonary system are among the leading causes of acute and chronic illness in the world. Pulmonary diseases or disorders may be organized into various categories, including, for example, obstructive diseases, restrictive diseases, infectious diseases, pulmonary vasculature disorders, pleural cavity disorders, and others. Pulmonary dysfunction may involve symptoms such as apnea, dyspnea, changes in blood or respiratory gases, symptomatic respiratory sounds, e.g., coughing, wheezing, respiratory insufficiency, and/or general degradation of pulmonary function, among other symptoms.

Obstructive pulmonary diseases can be associated with a decrease in the total volume of exhaled airflow caused by a narrowing or blockage of the airways. Examples of obstructive pulmonary diseases include asthma, emphysema, bronchitis, and chronic obstructive pulmonary disease (COPD). Restrictive pulmonary diseases involve a decrease in the total volume of air that the lungs are able to hold, which are often due to a decrease in the elasticity of the lungs themselves, or may be caused by a limitation in the expansion of the chest wall during inhalation. Pulmonary dysfunctions can also involve disorders of the pleural cavity and/or pulmonary vasculature, such as pulmonary hypertension, pulmonary edema, and pulmonary embolism. Pulmonary diseases may be caused by infectious agents such as viral and/or bacterial agents. Examples of infectious pulmonary diseases include pneumonia, tuberculosis, and bronchiectasis while non-infectious pulmonary diseases include lung cancer and adult respiratory distress syndrome (ARDS), for example.

The present disclosure provides solutions to these aforementioned skin diseases and disorders, pulmonary diseases and disorders, and other diseases and disorders by providing compositions of amniotic fluid.

SUMMARY OF THE INVENTION

Disclosed herein are compositions of amniotic fluid and methods of use. In one embodiment, the amniotic fluid is modified amniotic fluid. In one aspect are disclosed compositions comprising an amount of modified amniotic fluid wherein said amniotic fluid is sterilized and desalted.

In some embodiments, the administration device comprises a dual-chamber sprayer. In some embodiments, the administration device comprises a double syringe.

In some aspects, this disclosure provides methods for treating a pulmonary disease or disorder, the methods comprising administering to a patient in need thereof an amount of any of the above-mentioned compositions.

In some aspects, this disclosure provides methods for treating a gastrointestinal disease or disorder, the method comprising administering to a patient in need thereof an amount of any of the above-mentioned compositions.

In some aspects, this disclosure provides methods for treating a wound, the method comprising administering to a patient in need thereof an amount of any of the above-mentioned compositions. In some embodiments, the wound is a chronic wound. In other embodiments, the wound is an acute wound. In some embodiments, the composition is administered to the site of wound.

Disclosed herein are methods for treating a skin disease or disorder using compositions comprising amniotic fluid. In one aspect, the methods comprise administering to a patient in need thereof an effective amount of a composition comprising amniotic fluid.

In one aspect are disclosed methods for treating skin for cosmetic blemishes, the method comprising administering to a patient in need thereof an effective amount of a composition comprising amniotic fluid.

Also disclosed herein are methods for treating a pulmonary disease or disorder, the method comprising administering to a patient in need thereof an effective amount of a composition comprising amniotic fluid.

Also disclosed herein are methods for preventing or reducing scar formation on the spine or near the spine, or sealing a dural tear, the method comprising administering to a patient in need thereof an effective amount of a composition comprising amniotic fluid.

Also disclosed herein are methods for treating or preventing an anterior procedure or a modified anterior procedure, the method comprising administering to a patient in need thereof an effective amount of a composition comprising amniotic fluid.

Also disclosed herein are methods for enhancing wound healing or preventing scar formation as a result of a surgical incision, the method comprising administering to a patient in need thereof an effective amount of a composition comprising amniotic fluid.

Also disclosed herein are methods for reducing the amount of scar tissue in the reproductive system after a surgical procedure, the method comprising administering to a patient in need thereof an effective amount of a composition comprising amniotic fluid.

Also provided herein are systems comprising: a) a first composition comprising an amount of amniotic fluid; b) a second composition comprising an amount of a pharmaceutically acceptable carrier; and c) an administration device, comprising a first chamber having the first composition disposed therein, a second chamber having the second composition disposed therein, and one or more apertures configured to expel the first and second composition therefrom. In some embodiments, the administration device comprises a dual-chamber sprayer. In some embodiments, the administration device comprises a double syringe.

Also provided herein are any of the above compositions for use in treating a gastrointestinal disease or disorder, a skin disease or disorder, a patient who has undergone a cosmetic procedure, or a pulmonary disease or disorder; in preventing or reducing scar formation on the spine or near the spine, or sealing a dural tear; in treating or preventing an anterior procedure or a modified anterior procedure; in enhancing wound healing or preventing scar formation as a result of a surgical incision; or in reducing the amount of scar tissue in the reproductive system after a surgical procedure.

Also provided herein is the use of any of the above compositions in the preparation of a medicament for treating a gastrointestinal disease or disorder, a skin disease or disorder, a patient who has undergone a cosmetic procedure, or a pulmonary disease or disorder; in preventing or reducing scar formation on the spine or near the spine, or sealing a dural tear; in treating or preventing an anterior procedure or a modified anterior procedure; in enhancing wound healing or preventing scar formation as a result of a surgical incision; or in reducing the amount of scar tissue in the reproductive system after a surgical procedure.

DETAILED DESCRIPTION OF THE INVENTION

Figure 1:
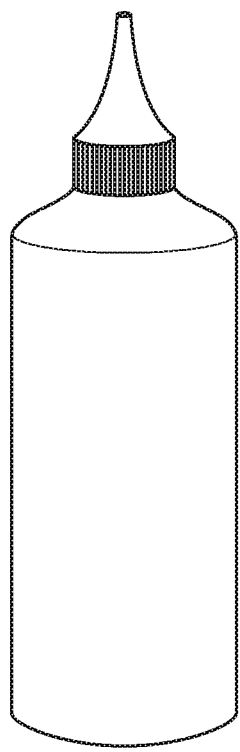
FIGS. 1-13 each schematically illustrate an embodiment of an administration apparatus used to administer one or both of a modified amniotic fluid composition and a pharmaceutically acceptable carrier.
Figure 2:
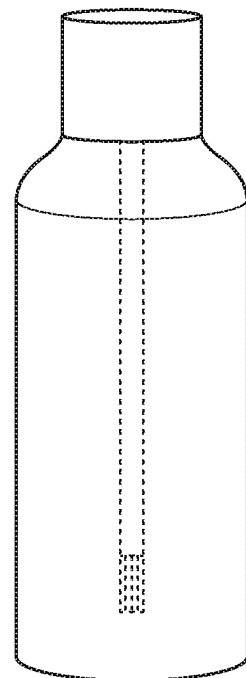

Disclosed herein are compositions of amniotic fluid and methods of use. In one embodiment, the amniotic fluid is modified amniotic fluid. In one aspect are disclosed compositions comprising an amount of modified amniotic fluid wherein said amniotic fluid is sterilized and desalted. In some embodiments, the modified amniotic fluid has been desalted to remove all or substantially all salts. In other embodiments, the modified amniotic fluid has a salt concentration of 0.9% saline+/−0.1%.

In some embodiments, the modified amniotic fluid is frozen. In some embodiments, the modified amniotic fluid is concentrated. In other embodiments, the modified amniotic fluid is lyophilized.

In some embodiments, the modified amniotic fluid is free or substantially free of material greater than 1 μm in size. In other embodiments, the amniotic fluid is free or substantially free of material greater than 0.5 μm in size.

In some embodiments, the modified amniotic fluid is human amniotic fluid.

In some embodiments, the modified amniotic fluid is free or substantially free of cells and/or cellular debris.

In some embodiments, the compositions disclosed herein further comprise a pharmaceutically acceptable carrier. In some embodiments, the modified amniotic fluid and pharmaceutically acceptable carrier have a weight ratio in the range between 1:100 and 100:1, between 1:50 and 50:1, between 1:40 and 40:1, between 1:30 and 30:1, between 1:25 and 25:1, between 1:20 and 20:1, between 1:15 and 15:1, between 1:10 and 10:1, between 1:5 and 5:1, or 1:1.

In some embodiments, the pharmaceutically acceptable carrier increases the viscosity of the amniotic fluid composition. In some embodiments, increasing the viscosity of the amniotic fluid. In some embodiments, the composition has a viscosity greater than 1.5 cP but less than 10,000 cP. In other embodiments, the composition has a viscosity greater than 75 cP but less than 7,000 cP. In yet other embodiments, the composition has a viscosity greater than 100 cP but less than 5,000 cP. All viscosities recited herein are measured at 25° C.

In some embodiments, the pharmaceutically acceptable carrier is an aqueous carrier. In some embodiments, the pharmaceutically acceptable carrier is Wharton's jelly, a biocompatible gelation agent, a polysaccharide, hyaluronic acid, poly-L-lysine, or collagen. In some embodiments, the pharmaceutically acceptable carrier is a preservative, for example, a polymeric preservative. In some embodiments, the collagen is human collagen, for example, human placental collagen. In some embodiments, the collagen is powderized.

In some embodiments, the composition is injectable. In other embodiments, the composition is a topical composition. In yet other embodiments, the composition is a liquid, gel, or paste.

In some aspects, provided herein are solid pellets comprising a dried droplet of the above-mentioned compositions. In some embodiments, the solid pellets have a diameter of from about 1 mm to about 5 mm.

In some aspects, provided herein are molded compositions comprising an amount of the above-mentioned compositions that have been dried in a mold.

In some aspects, provided herein are compositions of any of the above-mentioned compositions and a placental tissue graft. In some embodiments, the placental tissue graft is a dehydrated placental tissue graft.

In some aspects, provided herein are compositions of any of the above-mentioned compositions and an amount of micronized placental tissue particles.

In some aspects, this disclosure provides systems comprising: a first composition comprising an amount of any of the above-mentioned compositions; a second composition comprising an amount of a pharmaceutically acceptable carrier; and an administration device, comprising a first chamber having the first composition disposed therein, a second chamber having the second composition disposed therein, and one or more apertures configured to expel the first and second composition therefrom.

In some embodiments, the administration device comprises a dual-chamber sprayer. In some embodiments, the administration device comprises a double syringe.

In some aspects, this disclosure provides methods for treating a pulmonary disease or disorder, the methods comprising administering to a patient in need thereof an amount of any of the above-mentioned compositions. In some embodiments, the pulmonary disease or disorder is selected from the group consisting of pulmonary hypoplasia, respiratory distress syndrome, pneumothorax, chronic lung disease, asthma, emphysema, chronic obstructive pulmonary disease, and pneumonia. In some embodiments, the composition is administered to the site of pulmonary disease or disorder.

In some aspects, this disclosure provides methods for treating a gastrointestinal disease or disorder, the method comprising administering to a patient in need thereof an amount of any of the above-mentioned compositions. In some embodiments, the gastrointestinal disease or disorder is selected from the group consisting of intestinal atresia, irritable bowel syndrome (IBS), and constipation. In some embodiments, the composition is administered to the site of gastrointestinal disease or disorder. In some embodiments, the composition is administered orally via a capsule. In some embodiments, the capsule has an enteric coating. In some embodiments, the enteric coating is a delayed-release coating. In some embodiments, the enteric coating is designed to release all or most of the composition in the intestines.

In some aspects, this disclosure provides methods for treating a wound, the method comprising administering to a patient in need thereof an amount of any of the above-mentioned compositions. In some embodiments, the wound is a chronic wound. In other embodiments, the wound is an acute wound. In some embodiments, the composition is administered to the site of wound.

Disclosed herein are methods for treating a skin disease or disorder using compositions comprising amniotic fluid.

In one aspect are disclosed methods for treating a skin disease or disorder, the method comprising administering to a patient in need thereof an effective amount of a composition comprising amniotic fluid.

In some embodiments, the skin disease or disorder is selected from the group consisting of hives, poison ivy, rash, blisters, hemorrhoids, cutaneous T-cell lymphoma, plaque psoriasis, atopic dermatitis, eczema, and dermatitis.

In one aspect are disclosed methods for treating skin for cosmetic blemishes, the method comprising administering to a patient in need thereof an effective amount of a composition comprising amniotic fluid.

In some embodiments, the composition is applied to the skin after a cosmetic procedure. In one embodiment, the procedure is wrinkle reduction. In one embodiment, the procedure is scar reduction. In one embodiment, the procedure is pigmentation reduction. In one embodiment, the cosmetic procedure is laser skin resurfacing (lasabrasion, laser peel and laser vaporization), intense pulsed light, micro-needling (dermal needling), chemical peel, or microdermabrasion. In one embodiment, the composition is applied to skin after cosmetic surgery to reduce scarring.

In some embodiments, the composition is administered to the site of the skin disease or disorder.

Also disclosed herein are methods for treating a pulmonary disease or disorder, the method comprising administering to a patient in need thereof an effective amount of a composition comprising amniotic fluid.

In some embodiments, the pulmonary disease or disorder is selected from the group consisting of pulmonary hypoplasia, respiratory distress syndrome, pneumothorax, chronic lung disease, asthma, emphysema, pulmonary fibrosis, chronic obstructive pulmonary disease, and pneumonia. In some embodiments, the composition is administered to the site of pulmonary disease or disorder. In some embodiments, the composition is a liquid, gel, or paste. In some other embodiments, the composition is an injectable liquid or gel. In some other embodiments, the composition is a sprayable composition. In some other embodiments, the sprayable composition is employed in a nebulizer.

Also disclosed herein are methods for preventing or reducing scar formation on the spine or near the spine, or sealing a dural tear, the method comprising administering to a patient in need thereof an effective amount of a composition comprising amniotic fluid.

Also disclosed herein are methods for treating or preventing an anterior procedure or a modified anterior procedure, the method comprising administering to a patient in need thereof an effective amount of a composition comprising amniotic fluid. In an embodiment, the procedure is selected from the group consisting of Anterior Lumbar Interbody Fusion (ALIF) and Transforaminal Lumbar Interbody Fusion (TLIF).

Also disclosed herein are methods for enhancing wound healing or preventing scar formation as a result of a surgical incision, the method comprising administering to a patient in need thereof an effective amount of a composition comprising amniotic fluid.

Also disclosed herein are methods for reducing the amount of scar tissue in the reproductive system after a surgical procedure, the method comprising administering to a patient in need thereof an effective amount of a composition comprising amniotic fluid.

In some embodiments, the composition is administered to the site of the disease, disorder, surgical or cosmetic procedure, wound, scar formation, or dural tear.

In some embodiments, the composition is a topical composition. In other embodiments, the composition is a liquid, gel, or paste. In embodiments, the composition is an injectable gel. In embodiments, the composition is a sprayable composition.

In some embodiments, the amniotic fluid has been concentrated. In some embodiments, the amniotic fluid is lyophilized.

In some embodiments, the composition further comprises a pharmaceutically acceptable carrier, for example, an aqueous carrier. In some embodiments, the pharmaceutically acceptable carrier is Wharton's jelly, a biocompatible gelation agent, a polysaccharide, hyaluronic acid, poly-L-lysine, or collagen.

In some embodiments, the pharmaceutically acceptable carrier is a preservative, for example, a polymeric preservative.

In some embodiments, the collagen is human collagen, for example, human placental collagen. In other embodiments, the collagen is powderized.

In some embodiments, the composition further comprises an amount of micronized placental tissue particles.

In some embodiments, the amniotic fluid and the pharmaceutically acceptable carrier are mixed immediately prior to use. In some embodiments, the compositions provided herein become a solid, a semi-solid, or a gel after application to a subject.

Also provided herein are systems comprising: a) a first composition comprising an amount of amniotic fluid; b) a second composition comprising an amount of a pharmaceutically acceptable carrier; and c) an administration device, comprising a first chamber having the first composition disposed therein, a second chamber having the second composition disposed therein, and one or more apertures configured to expel the first and second composition therefrom. In some embodiments, the administration device comprises a dual-chamber sprayer. In some embodiments, the administration device comprises a double syringe.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated by reference to disclose and describe the methods and/or materials in connection with which the publications are cited.

All numerical designations, e.g., pH, temperature, time, concentration, and molecular weight, including ranges, are approximations which are varied (+) or (−) by increments of 0.1 or 1.0, where appropriate. It is to be understood, although not always explicitly stated that all numerical designations are preceded by the term "about." It also is to be understood, although not always explicitly stated, that the reagents described herein are merely exemplary and that equivalents of such are known in the art.

Definitions

As used herein the following terms have the following meanings.

It must be noted that as used herein and in the appended claims, the singular forms "a," "an," and "the" include plural referents unless the context clearly dictates otherwise. Thus, for example, reference to "a pluripotent stem cell" includes a plurality of pluripotent stem cells.

The term "about" when used before a numerical designation, e.g., temperature, time, amount, concentration, and such other, including a range, indicates approximations which may vary by (+) or (−) 10%, 5% or 1%.

"Comprising" or "comprises" is intended to mean that the compositions, for example media, and methods include the recited elements, but does not exclude others. "Consisting essentially of" when used to define compositions and methods, shall mean excluding other elements of any essential significance to the combination for the stated purpose. Thus, a composition consisting essentially of the elements as defined herein would not exclude other materials that do not materially affect the basic and novel characteristic(s) of the claimed composition. A method consisting essentially of the steps as defined herein would not exclude other steps that do not materially affect the basic and novel characteristic(s) of the claimed method. "Consisting of" shall mean excluding more than trace elements of other ingredients and substantial method steps. Embodiments defined by each of these transition terms are within the scope of this invention.

"Optional" or "optionally" means that the subsequently described event or circumstance can or cannot occur, and that the description includes instances where the event or circumstance occurs and instances where it does not.

"Administration" refers to introducing an agent, such as a composition comprising modified amniotic fluid, into a patient. Typically, an effective amount is administered, which amount can be determined by the treating physician or the like. Any route of administration, such as oral, topical, subcutaneous, peritoneal, intra-arterial, inhalation, vaginal, rectal, nasal, or instillation into body compartments can be used. The agent, such as a composition of modified amniotic fluid, may be administered by direct blood stream delivery, e.g. sublingual, buccal, intravenous, intranasal, or intrapulmonary administration. In preferred embodiments, the agent is administered intravenously or subcutaneously.

The related terms and phrases "administering" and "administration of," when used in connection with an agent (and grammatical equivalents) refer both to direct administration, which may be administration to a patient by a medical professional or by self-administration by the patient, and/or to indirect administration, which may be the act of prescribing an agent. For example, a physician who instructs a patient to self-administer an agent and/or provides a patient with a prescription for an agent is administering the agent to the patient.

The term "subject" as used herein is any vertebrate organism including but not limited to mammalian subjects such as humans, farm animals, domesticated pets and the like. The term "patient" may be used interchangeably with "subject."

The term "amnion" as used herein includes amniotic membrane where the intermediate tissue layer is intact or has been substantially removed.

The term "placental tissue" refers to any and all of the well-known components of the placenta and umbilical cord including but not limited to amnion, chorion, Wharton's Jelly, and the like. In one preferred embodiment, the placental tissue does not include any of the umbilical cord components (e.g., Wharton's jelly, umbilical cord vein and artery, and surrounding membrane).

The term "treatment" or "treating," to the extent it relates to a disease or condition, includes preventing the disease or condition from occurring, inhibiting the disease or condition, eliminating the disease or condition, and/or relieving one or more symptoms of the disease or condition.

The term "biocompatible" as used herein refers to a material that is suitable for administration to a subject, such as application topically to or implantation or injection into the subject. In various aspects, a biocompatible material does not cause unacceptable toxic or injurious effects once administered to the subject.

The term "biocompatible gelation agent" refers to any agent that is liquid prior to application to a wound or tissue (e.g., at room temperature or colder, or prior to exposure to air) and is or becomes a gel, semi-solid, or solid after application (e.g., at body temperature or after exposure to air). Nonlimiting examples are provided below.

As used herein, the terms "skin disease or disorder" encompass any disease or other disorder affecting the skin of a subject. Such skin diseases or disorders include, for example: acne, atopic dermatitis, blisters, cutaneous T-cell lymphoma, dermatitis, eczema, erythroderma, impetigo, hemorrhoids, hives, keratosis, lupus, plaque psoriasis, poison ivy, prurigo, rash, Saint Anthony's fire, and seborrhea.

As used herein, the term "pulmonary disease or disorder" refers to any pathology affecting at least in part the lungs or respiratory system. The term encompasses obstructive and non-obstructive pulmonary diseases or disorders, for instance, asthma, emphysema, chronic obstructive pulmonary disease, pulmonary adema, pulmonary hypoxia, pneumonia, tuberculosis, mixed connective tissue disease, and fibrosis in all its forms (including idiopathic pulmonary fibrosis). The term applies particularly to pulmonary eosinophilic diseases or disorders, e.g., eosinophilic asthma.

As used herein, the terms "gastrointestinal disease or disorder" encompass any disease or other disorder of the gastrointestinal tract of a subject. Such gastrointestinal diseases or disorders include, for example: disorders not manifested by presence of ulcerations in the intestinal atresia, irritable bowel syndrome, constipation, gastric mucosa, including chronic or atrophic gastritis, gastroenteritis, non-ulcer dyspepsia, esophogeal reflux disease and gastric motility disorders, peptic ulcer disease (e.g., gastric and duodenal ulcers). In addition, "gastrointestinal disease or disorder" refers to such disorders of the upper gastrointestinal tract caused or mediated by bacteria.

An "effective amount" refers to at least an amount effective, at dosages and for periods of time necessary, to achieve the desired therapeutic or prophylactic result. An effective amount can be provided in one or more administrations.

A "therapeutically effective amount" is at least the minimum concentration required to effect a measurable improvement of a particular disease or disorder. A therapeutically effective amount herein may vary according to factors such as the disease state, age, sex, and weight of the patient.

The term "amniotic fluid," unless specified otherwise, refers to the entire fluid and non-fluid components present in the amniotic cavity, such as the liquid, solid, semi-solid, or cellular constituents contained therein, whether in suspension or not. "Modified amniotic fluid" is used to specify amniotic fluid that differs from amniotic fluid found in nature. In some embodiments, the modified amniotic fluid has some components (solvent, growth factors, amino acids, salts, proteins, and the like) removed from the amniotic fluid. In other embodiments, the modified amniotic fluid has some components (solvent, growth factors, amino acids, salts, proteins, and the like) added to the amniotic fluid. In yet other embodiments, the modified amniotic fluid has some components (solvent, growth factors, amino acids, salts, proteins, and the like) removed from the amniotic fluid and has some components (solvent, growth factors, amino acids, salts, proteins, and the like) added to the modified amniotic fluid.

The term "full term" is used to describe a stage during human pregnancy that is at least 38 gestational weeks.

The term "post term" is used to describe a stage during human pregnancy that is greater than 41 gestational weeks.

The term "viscosity" is used to refers to the internal resistance to flow exhibited by a fluid at a specified temperature; the ratio of shearing stress to rate of shear. A liquid has a viscosity of one poise if a force of 1 dyne/square centimeter causes two parallel liquid surfaces one square centimeter in area and one square centimeter apart to move past one another at a velocity of 1 cm/second. One poise equals one hundred centipoise. As viscosity is temperature dependent, the units of viscosity also refer to the temperature related thereto.

The term "dosage form" refers to any solid object, semi-solid, or liquid composition designed to contain a specific pre-determined amount (i.e. dose) of a certain active ingredient. Suitable dosage forms may be pharmaceutical drug delivery systems, including those for oral administration, buccal administration, rectal administration, topical, transdermal, or mucosal delivery or subcutaneous implants, or other implanted drug delivery systems and the like.

A composition that is "substantially free" of a substance means, in one aspect, that the amount of the substance in the composition is so low that it does not materially affect the composition or the use thereof. In another aspect, a composition that is "substantially free" of a substance means that ≥90%, ≥95%, or ≥99% of the substance has been removed from the composition.

It is understood that where a parameter range is provided, all integers within that range, and tenths and hundredths thereof, are also provided by the invention. For example, "5-10%" includes 5%, 6%, 7%, 8%, 9%, and 10%; 5.0%, 5.1%, 5.2% . . . 9.8%, 9.9%, and 10.0%; and 5.00%, 5.01%, 5.02% . . . 9.98%, 9.99%, and 10.00%.

For the foregoing embodiments, each embodiment disclosed herein is contemplated as being applicable to each of the other disclosed embodiments. All combinations, sub-combinations, and permutations of the various elements of the methods described herein are envisaged and are within the scope of the invention.

Amniotic Fluid

Amniotic fluid originates predominantly from maternal plasma that crosses the amniotic membranes into the amniotic cavity. Amniotic fluid is a dynamic composition that undergoes changes throughout pregnancy and is made up of water and soluble materials such as, for example, electrolytes, carbohydrates, proteins, amino acids, lactate, pyruvate, hormones, growth factors, cytokines, and other bioactive molecules. In humans, fetal urine begins to enter the amniotic fluid at approximately 8-11 weeks gestation and becomes the major component of amniotic fluid during the second half of pregnancy. In addition, a heterogeneous population of cells derived from fetal skin, gastrointestinal, respiratory, and urinary tracts and the amniotic membrane all slough off into the amniotic fluid. Stem cells have been isolated from amniotic fluid including, for example, pluripotent amniotic fluid stem cells, placental-derived stem cells, and mesenchymal stem cells. Prior to keratinization of fetal skin there is rapid bi-directional diffusion between the fetus and the amniotic fluid. Thus, the amniotic fluid components can vary drastically depending on the gestational age from which the amniotic fluid sample is collected.

Amniotic fluid is required for normal lung development. Too little fluid for long periods may cause abnormal or incomplete development of the lungs. Fetal lung liquid is also present in the amniotic fluid.

In humans, amniotic fluid volume varies during gestation. At around 10 weeks gestation the volume of amniotic fluid is approximately 25 mL. At around 20 weeks gestation, the volume is approximately 400 mL. The volume of amniotic fluid plateaus at approximately 800 mL at around 29 weeks gestation and declines to approximately 400 mL at full term.

Amniotic fluid contains high levels of taurine. Taurine has many fundamental biological roles, such as conjugation of bile acids, antioxidation, osmoregulation, membrane stabilization and modulation of calcium signaling. Amniotic fluid is also known to contain glutamine which is an essential precursor for nucleic acid biosynthesis in cells and is particularly important in rapidly dividing cells such as intestinal mucosa cells. Another component of amniotic fluid is arginine. Arginine and its derivatives are key regulators of placental angiogenesis, trophoblast growth and embryogenesis. Polyamines, a derivative of arginine, support proliferation and differentiation of intestinal epithelial cells.

Amniotic fluid is also made up of growth factors, for example, transforming growth factor alpha (TGF-α), transforming growth factor beta (TGF-β), insulin-like growth factors I (IGF-I), erythropoietin (EPO), granulocyte colony-stimulating factor (G-CSF), and vascular endothelial growth factor (VEGF) play a role in fetal growth and development. In addition, epithelial growth factor (EGF) has been shown to play a role in improving lung maturity, reversing the effects of esophageal ligation, and increasing small intestine length.

In humans, the fetal amniotic fluid sodium concentration is approximately 135 mEq/l and the potassium concentration is approximately 5 mEq/l at between 32-39 weeks gestation. Approximately 2% of the amniotic fluid is composed of inorganic and organic salts.

The amniotic fluid can be collected by any means known in the art (e.g., in U.S. Application Publication No. 2015/0025366, filed Oct. 7, 2014 and PCT Publication No. WO 2014/140913, filed Mar. 14, 2014). The contents of each of these applications are specifically incorporated by reference in their entireties. The amniotic fluid can be collected from a mammal, for example, a human. The amniotic fluid can be collected from any stage of pregnancy following its development after the appearance of the amniotic cavity, which occurs for humans approximately 7-8 days after fertilization. In some embodiments, the amniotic fluid is collected from a full-term pregnancy. In other embodiments, the amniotic fluid is collected from a post-term pregnancy. In some embodiments, the amniotic fluid is collected pre-Caesarean method. In other embodiments, the amniotic fluid is collected pre-natural birth. In other embodiments, the amniotic fluid is collected after birth. The amniotic fluid can be from a single source or amniotic fluid can be pooled from multiple sources. In preferred embodiments, the amniotic fluid is from a single source.

In some embodiments, the amniotic fluid is modified amniotic fluid such that it differs from naturally occurring amniotic fluid. Any method known by one of skill in the art can be used to modify the amniotic fluid. In some embodiments, the modified amniotic fluid is sterilized and desalted.

In some embodiments, the amniotic fluid is sterilized. The amniotic fluid can be sterilized by any method known to those of skill in the art. Sterilization may be accomplished, for example, by filtration through a low protein-binding membrane filter of about 0.1-1.0 μm pore size (available commercially, for example, from Millipore, Billerica, Mass., USA) after collecting the amniotic fluid. Autoclaving or other elevated temperature-based methods of sterilization are not favored, since many of the components of the present amniotic fluid are heat labile and will be irreversibly degraded by temperatures such as those achieved during most heat sterilization methods. In some embodiments, the amniotic fluid is free or substantially free of material greater than 1 μm in size. In other embodiments, the amniotic fluid is free or substantially free of material greater than 0.5 μm in size.

In some embodiments, the modified amniotic fluid has been desalted. In some embodiments, the modified amniotic fluid has been desalted to remove all or substantially all salts. In other embodiments, the modified amniotic fluid has been desalted to a salt concentration of 0.9% saline+/−0.1%. The modified amniotic fluid can be desalted using any method known by those of skill in the art including, for example, gel filtration chromatography or dialysis.

In some embodiments, the modified amniotic fluid has been denitrified to remove nitrogen compounds dissolved in the amniotic fluid. Any method known to one of skill in the art can be used to remove nitrogen compounds, including, for example, by means of chemicals, ion exchange, reversed osmosis, biological denitrification (e.g., microorganisms).

In some embodiments, the modified amniotic fluid is free or substantially free of cells and/or cellular debris. Methods for removing cells are well known to those of skill in the art, for example, centrifugation, fractionation, or filtration. In some embodiments, the amniotic fluid components are separated into component parts by, for example, affinity chromatography. Those of skill in the art are familiar with techniques for removing cells and/or cellular debris from biological samples. Examples of such techniques include but are not limited to centrifugation (e.g. at a speed in the range of from about 1000 rpm to about 5000 rpm, and preferably at least about 1800 rpm). In one embodiment of the invention, all or substantially all of the cells and/or cellular debris is removed from a sample of amniotic fluid by centrifugation at about 1800 rpm. In some embodiments, the amniotic fluid has been concentrated.

In some embodiments, the modified amniotic fluid and/or amniotic fluid has been concentrated. Any method known to those of ordinary skill in the art can be used to concentrate the amniotic fluid.

In some embodiments, the modified amniotic fluid and/or amniotic fluid described herein can be lyophilized (e.g., freeze-dried) to promote stability, preserve activity and increase shelf-life. One skilled in the art would understand how to reconstitute the lyophilized product before use. In some embodiments, the modified amniotic fluid is free or substantially free of cells and/or cellular debris prior to lyophilization.

In some embodiments, the modified amniotic fluid and/or amniotic fluid is used immediately after collection. In other embodiments, the amniotic fluid is cryopreserved (e.g. frozen), for example, using any cryopreservation techniques well-known to those skilled in the art. In some embodiments, the amniotic fluid is modified prior to cryopreservation. In other embodiments, the amniotic fluid is modified after cryopreservation. In some embodiments, all or substantially of the cells and/or cellular debris are removed from the amniotic fluid prior to cryopreservation. In some embodiments, all or substantially of the cells and/or cellular debris are removed from the amniotic fluid after cryopreservation.

Alternatively, the modified amniotic fluid and/or amniotic fluid concentrates may be stored as sterile compositions. The modified amniotic fluid and/or amniotic fluid concentrates may be used as such or they can then be mixed under aseptic conditions with a sterile diluent to produce a concentrated 1× sterile medium formulation.

In some embodiments, the amniotic fluid is collected from a mammal, for example, a human or non-human mammals such as a bovine, an ovine, or a porcine.

In some embodiments, the modified amniotic fluid and/or amniotic fluid is used in an autologous therapy. In some embodiments, the modified amniotic fluid and/or amniotic fluid is used in an allogenic therapy. In yet other embodiments, the modified amniotic fluid and/or amniotic fluid is used in a xenogenic therapy. In some embodiments, the amniotic fluid is collected from the same or different source as the pharmaceutically acceptable carrier, placental tissue graft, micronized placental tissue, placental tissue extracts, or combination thereof.

Pharmaceutically Acceptable Carrier

The present disclosure provides compositions of modified amniotic fluid and compositions of amniotic fluid. In some embodiments the modified amniotic fluid and/or amniotic fluid compositions further comprise a pharmaceutically acceptable carrier. In some embodiments, more than one pharmaceutically acceptable carrier can be used. Any pharmaceutically acceptable carrier known to those of skill in the art can be used. In some embodiments, the pharmaceutically acceptable carrier is an aqueous carrier, for example, Wharton's jelly, a biocompatible gelation agent, a polysaccharide, hyaluronic acid, poly-1-lysine, or collagen.

In some embodiments the collagen is human collagen, for example, human placental collagen. In other embodiments, the collagen is powderized.

In some embodiments, the pharmaceutically acceptable carrier is a preservative, for example, a polymeric preservative.

In some embodiments, the pharmaceutically acceptable carrier is selected from the group consisting of a polyethylene glycol (PEG)(e.g., PEG 150 Distearate), honey, a large molecular weight protein (e.g., bovine serum albumin or soy protein), polyvinyl alcohol, glyceryl monostearate, hyaluronic acid, glycerin, preferably vegetable-derived, proteins, preferably hydrolyzed proteins, (e.g., soy protein and silk protein), vasoline, citrosept, parabens, xanthan gum, i-carregaan, phytagel, Carbopol® polymers, and polyvinyl pyrrolidone.

Biocompatible gelation agents include thermosensitive sol-gel reversible hydrogels such as aqueous solutions of poloxamers. In one aspect, the poloxamer is a nonionic triblock copolymer composed of a central hydrophobic chain of polyoxypropylene (e.g., (poly(propylene oxide)) flanked by two hydrophilic chains of polyoxyethylene (e.g., poly(ethylene oxide)). In one aspect, the poloxamer has the formula

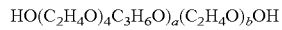

$$HO(C_2H_4O)_4C_3H_6O)_a(C_2H_4O)_bOH$$

wherein a is from 10 to 100, 20 to 80, 25 to 70, or 25 to 70, or from 50 to 70; b is from 5 to 250, 10 to 225, 20 to 200, 50 to 200, 100 to 200, or 150 to 200. In another aspect, the poloxamer has a molecular weight from 2,000 to 15,000, 3,000 to 14,000, or 4,000 to 12,000. Poloxamers useful herein are sold under the tradename Pluronic® manufactured by BASF. Non-limiting examples of poloxamers useful herein include, but are not limited to, Pluronic® F68, P103, P105, P123, F127, and L121.

In one aspect, the biocompatible gelation agent is an agent that is liquid prior to application to a subject (e.g., at room temperature or colder) and becomes a gel after application to the subject (e.g., at body temperature). In one embodiment, the biocompatible gelation agent is a hydrogel.

In another aspect, disclosed herein is a composition comprising modified amniotic fluid and a poloxamer wherein the composition is in a sol (liquid) phase at about 0° C. to about 20° C. and is in a gel (solid) phase at or near the body temperature or higher, such as about 25° C. to about 40° C., or about 30° C. to about 37° C.

In some aspects, the pharmaceutically acceptable carrier is a pharmaceutically acceptable aqueous carrier such as water or an aqueous carrier. Examples of pharmaceutically acceptable aqueous carrier include sterile water, saline, phosphate buffered saline, aqueous hyaluronic acid, Ringer's solution, dextrose solution, Hank's solution, and other aqueous physiologically balanced salt solutions.

Nonaqueous pharmaceutically acceptable carriers include fixed oils, vegetable oils such as olive oil and sesame oil, triglycerides, propylene glycol, polyethylene glycol, and injectable organic esters such as ethyl oleate can also be used. Examples of oils also include fats; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate.

The pharmaceutically acceptable carrier can also contain minor amounts of additives, such as substances that enhance isotonicity, chemical stability, or cellular stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. In some aspect, the composition has a pH in the physiological pH range, such as pH 7 to 9. In some embodiments, dimethyl sulfoxide (DMSO) has been added to the modified amniotic fluid.

In some embodiments, the carrier includes one or more humectants, thickening agents, antioxidants, chelating agents, buffers, and preservatives.

Examples of solvents include $C_2$-$C_{10}$ alcohols, such as hexanol, cyclohexanol, benzyl alcohol, 1,2-butanediol, glycerol, and amyl alcohol; $C_5$-$C_{10}$ hydrocarbons such as n-hexane, cyclohexane, and ethylbenzene; $C_4$-$C_{10}$ aldehydes and ketones, such as heptylaldehyde, cyclohexanone, and benzylaldehyde; $C_4$-$C_{10}$ esters, such as amyl acetate and benzyl propionate; ethereal oils, such as oil of *eucalyptus*, oil of rue, cumin oil, limonene, thymol, and 1-pinene; halogenated hydrocarbons having 2-8 carbon atoms, such as 1-chlorohexane, 1-bromohexane, and chlorocyclohexane.

Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate.

Examples of humectants include glycerin, 1,3-butylene glycol, and propylene glycol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

In one aspect, depending on the type of pharmaceutically acceptable carrier used, the composition described herein can comprise about 0.1-99.9%, 0.1-50%, or 0.1-30%, such as 0.1%, 0.25%, 0.5%, 0.75%, 1%, 2%, 5%, 7%, 10%, 15%, 20%, 25%, 30%, 40%, 45%, 50%, 55%, 60%, 65%, 70%, 75%, 80%, 85%, 90% or 95% of the pharmaceutically acceptable carrier used in the total weight of the composition, or any range between two of the numbers (end point inclusive).

In some embodiments, any one of the above listed pharmaceutically acceptable carriers is expressly excluded.

In some embodiments, the composition is formulated for topical use. The topical formulations may further include one or more of the wide variety of agents known to be effective as skin penetration enhancers. Examples of these are 2-pyrrolidone, N-methyl-2-pyrrolidone, dimethylacetamide, dimethylformamide, propylene glycol, alcohol, dimethyl sulfoxide, and Azone. Additional agents may further be included to make the formulation cosmetically acceptable. Examples of these are fats, waxes, oils, dyes, fragrance, preservatives, stabilizers, and surface active agents. Keratolytic agents such as those known in the art may also be included. Examples are salicyclic acid, sulfur, transretinoic acid and later generations of retinoids. The amounts of each of these various types of additive will be readily apparent to those skilled in the art, optimal amounts being the same as in other, known formulations designed for the same type of administration. Stratum corneum penetration enhancers, for example, will typically be included at levels within the range of about 0.1% to about 30% by weight, preferably from about 1% to about 15%.

In some embodiments, the compositions are formulated as a lotion or a cream containing from about 0.001% to 99%, or from about 1% to about 20%, or from about 5% to about 10% of the amniotic fluid or amniotic fluid components described herein.

Placental Tissue

As will be understood by one of skill in the art, in some embodiments the compositions and methods of treatment described herein comprise placental tissue, for example, a placental tissue graft, micronized placental tissue particles, or both in addition to the modified amniotic fluid and optional pharmaceutical acceptable carrier.

Placental tissue grafts and methods of preparing the tissue grafts are described, e.g., in U.S. Pat. No. 8,372,437, filed Aug. 17, 2007 and U.S. Pat. No. 8,357,403, filed Sep. 8, 2008 and continuing applications therefrom, as well as PCT Publication No. WO 2009/033160, filed Sep. 8, 2008. The contents of each of these applications are specifically incorporated by reference in their entireties.

In some embodiments, an amount of modified amniotic fluid is added to a placental tissue graft, for example, a dehydrated tissue graft to form a rehydrated tissue graft. The rehydrated tissue graft is then dehydrated. Without being bound by theory, it is believed that such a process would create a modified tissue graft having a higher concentration of components found in amniotic fluid (e.g., growth factors, cytokines, amino acids).

Micronized placental components and methods of preparing the micronized placental components are described, e.g., in PCT Publication No. WO 2012/112410, filed Feb. 13, 2012, U.S. Patent Application Pub. No. 2014/0050788, filed Aug. 9, 2013, as well as U.S. patent application Ser. No. 14/718,703, filed May 21, 2015, and Ser. No. 14/793,673, filed Jul. 7, 2015. The contents of each of these applications are specifically incorporated by reference in their entireties.

Compositions and methods of preparing placental tissue grafts further comprising micronized placental tissue components are described, e.g., in U.S. Patent Application Pub. No. 2014/0052274, filed Mar. 15, 2013. The contents of which is specifically incorporated by reference in its entirety.

Extracts from micronized placental components are described in, e.g., U.S. Patent Application Pub. No. 2014/0050788. In some aspects, the extracts comprise the growth factors and/or cytokines of the amnion, chorion, intermediate tissue layer, umbilical cord component(s), or any combination thereof. In one aspect, the extract is a saline extract, a sterile water extract, or an extract using any suitable buffer known in the art, of the micronized placental components.

The amount of micronized composition in a specified case will vary according to the specific compound being utilized, the particular compositions formulated, the mode of application, and the particular situs and subject being treated. In one aspect, the micronized composition is from 0.5% to 20%, 1% to 10%, 2% to 5%, or about 3% by weight of the composition, or any range between two of the numbers (end point inclusive).

In one aspect, the extract from micronized composition is from 0.5% to 20%, 1% to 10%, 2% to 5%, or about 3% by weight of the composition, or any range between two of the numbers (end point inclusive).

In a related aspect, separation of the extract is conducted such that the remaining micronized placental components still contain a significant amount of growth factors.

In a further aspect, the composition comprises micronized amnion. In another aspect, the composition comprises micronized amnion and micronized intermediate tissue layer. In another aspect, the composition comprises micronized amnion and micronized chorion. In another aspect, the composition comprises a micronized tissue graft comprising two or more layers, wherein the layers are amnion, chorion, intermediate layer, and any combination thereof.

Additional Components

In a further aspect, the composition comprises bone. In some embodiments, an amniotic fluid composition as described herein is combined with bone, bone chips, demineralized bone matrix, and the like. Bone may be from any source, including allogenic, from a cadaver, from an animal (preferably a mammal, e.g., pig, cow, and the like), or autologous (from the patient being administered the composition). In some embodiments, the bone is synthetic bone. The composition comprising bone may be used, for example, in bone grafting, dental implant, and the like.

Formulations

In some aspects, the composition is injectable. In other aspects the composition is a topical composition. In yet other embodiments, the compositions is a liquid, gel, or paste. In some embodiments, the compositions is a sprayable composition wherein the composition is employed by, for example, a nebulizer.

Formulations for topical administration can include, emulsions, creams, aqueous solutions, oils, ointments, putty, pastes, gels, lotions, milks and suspensions.

The compositions can also include additional components typically present in such compositions. In one aspect, the topical composition can include one or more of the following components: fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, swelling agents, insect repellents, hydrotropes, solubilizers, preservatives, perfume oils and dyes. Examples of each of these components are disclosed in U.S. Pat. No. 8,067,044, which is incorporated by reference with respect these components.

In one embodiment, the composition comprises 0.001%-100% amniotic fluid or amniotic fluid components, including 0.01%, 0.1%, 1%, 5%, 10%, 15%, 20%, 25%, 30%, 35%, 40%, 45%, 50%, 55%, 60%, 65%, 70%, 75%, 80%, 85%, 90%, or 95% amniotic fluid or amniotic fluid components. In embodiments, the composition comprises 0.01%-95%, 0.1%-90%, 1%-85%, 5%-80%, 10%-75%, 15%-70%, 20%-65%, 25%-60%, 30%-55%, 35%-50%, or 40%-45% amniotic fluid or amniotic fluid components.

In one aspect, the composition can include one or more surfactants. Surfactants (or surface-active substances) that may be present are anionic, non-ionic, cationic and/or amphoteric surfactants. Typical examples of anionic surfactants include, but are not limited to, soaps, alkylbenzenesulfonates, alkanesulfonates, olefin sulfonates, alkyl ether sulfonates, glycerol ether sulfonates, alpha-methyl ester sulfonates, sulfo fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, e.g. acyl lactylates, acyl tartrates, acyl glutamates and acyl aspartates, alkyl oligoglucoside sulphates, protein fatty acid condensates (in particular wheat-based vegetable products) and alkyl (ether) phosphates. Examples of non-ionic surfactants include, but are not limited to, fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. Examples of amphoteric or zwitterionic surfactants include, but are not limited to, alkylbetaines, alkylamidobetaines, aminopropionates, aminoglycinates, imidazolinium-betaines and sulfobetaines.

In one aspect, the surfactant can be fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, alpha-olefinsulfonates, ether carboxylic acids, alkyl oligoglucosides, fatty acid glucamides, alkylamidobetaines, amphoacetals and/or protein fatty acid condensates.

Examples of zwitterionic surfactants include betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethyl-carboxymethyl glycinate.

In one aspect, the emulsifier can be a nonionogenic surfactant selected from the following: addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical; alkyl and/or alkenyl oligoglycosides having 8 to 22 carbon atoms in the alk(en)yl radical and the ethoxylated analogs thereof; addition products of from 1 to 15 mol of ethylene oxide onto castor oil and/or hydrogenated castor oil; addition products of from 15 to 60 mol of ethylene oxide onto castor oil and/or hydrogenated castor oil; partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide; partial esters of polyglycerol (average degree of self-condensation 2 to 8), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide; mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof; wool wax alcohols; polysiloxane-polyalkyl-polyether copolymers and corresponding derivatives; and block copolymers, e.g. polyethylene glycol-30 dipolyhydroxystearates. In one aspect, the emulsifier is a polyalkylene glycol such as, for example, polyethylene glycol or polypropylene glycol. In another aspect, the emulsifier is polyethylene glycol having a molecular weight 100 Da to 5,000 Da, 200 Da to 2,500 Da, 300 Da to 1,000 Da, 400 Da to 750 Da, 550 Da to 650 Da, or about 600 Da.

In some aspects, the modified amniotic fluid and the pharmaceutically acceptable carrier are mixed immediately prior to use. In other embodiments, the modified amniotic fluid and pharmaceutically acceptable carrier are mixed together prior to use for a period of time such as thirty minutes, one hour, two hours, three hours, five hours, six hours, twelve hours, twenty-four hours, forty-eight hours or longer prior to use. In some embodiments, the composition becomes a solid, a semi-solid, or a gel after application to a subject.

In some aspects, the amniotic fluid and the pharmaceutically acceptable carrier are mixed immediately prior to use. In other embodiments, the amniotic fluid and pharmaceutically acceptable carrier are mixed together prior to use for a period of time such as thirty minutes, one hour, two hours, three hours, five hours, six hours, twelve hours, twenty-four hours, forty-eight hours or longer prior to use. In some embodiments, the composition becomes a solid, a semi-solid, or a gel after application to a subject.

In one aspect, the composition is a solid pellet comprising a dried droplet of an amount of modified amniotic fluid and an amount of a pharmaceutically acceptable carrier. In some embodiments, the solid pellet has a diameter of from about 1 mm to about 5 mm.

In one aspect, the composition comprise an amount of the composition of modified amniotic fluid and an amount of a pharmaceutically acceptable carrier dried in a mold.

Methods of Use

The compositions as described herein can be used in numerous medical applications involving treating or preventing a skin disease or disorder, a pulmonary disease or disorder, a gastrointestinal disease or disorder, or a wound.

In one aspect, the modified amniotic fluid and/or compositions can be used for treating or preventing a pulmonary disease or disorder. In some embodiments, the pulmonary disease or disorder is selected from the group consisting of pulmonary fibrosis, pulmonary hypoplasia, respiratory distress syndrome, pneumothorax, chronic lung disease, asthma, emphysema, chronic obstructive pulmonary disease, and pneumonia. In some embodiments, the modified amniotic fluid and/or amniotic fluid composition is administered to the site of pulmonary disease or disorder. The modified amniotic fluid and/or amniotic fluid composition can be delivered to the lungs by any delivery method known by one of skill in the art. The modified amniotic fluid and/or amniotic fluid may be administered in a bolus dose of liquid into the lungs of the patient. In some embodiments, the modified amniotic fluid and/or amniotic fluid compositions are administered by a metered dose inhaler or a dry powder inhaler. In some embodiments, the modified amniotic fluid and/or amniotic fluid composition is administered in a weight-independent or weight-dependent dosage.

In preferred methods, the modified amniotic fluid and/or amniotic fluid compositions can be administered by a nebulizer. Nebulizers provide a means of administering drugs to the airways of a patient whilst the patient breathes at an approximately normal rate. They are particularly suitable for patients who are unable, whether due to age or injury or otherwise, to inhale at the much higher rates required for administration of drugs via metered dose inhalers or dry powder inhalers and for patients who cannot for whatever reason coordinate the activation of the metered dose inhaler with their inhalation of breath. The nebulizer apparatus creates a vapor containing modified amniotic fluid and/or amniotic fluid particles and the patient breathes the vapor via a mouthpiece or mask attached to the nebulizer. In some embodiments, the modified amniotic fluid and/or amniotic fluid composition is administered in a weight-independent or weight-dependent dosage.

A nebulized solution of a modified amniotic fluid and/or amniotic fluid composition is one dispersed in air to form an aerosol, and a nebulizer generates very fine liquid droplets suitable for inhalation into the lung. Nebulizers typically use compressed air, ultrasonic waves, or a vibrating mesh to create a mist of the droplets and may also have a baffle to remove larger droplets from the mist by impaction. A variety of nebulizers are available for this purpose, such as ultrasonic nebulizers, jet nebulizers and breath-actuated nebulizers. In use, mouthpieces or masks are typically attached to a patient to aid delivery of the nebulized solution.

In preferred embodiments, formulations of modified amniotic fluid and/or amniotic fluid are for delivery with and patients are treated using a high efficiency nebulizer, in particular one that can deliver at least 15%, preferably at least 25%, more preferably at least 35% of the drug substance to the patient's lungs.

In specific embodiments of the invention, formulations of modified amniotic fluid and/or amniotic fluid are delivered using a high efficiency jet nebulizer, a high efficiency ultrasonic nebulizer or a high efficiency vibrating mesh nebulizer, use of these devices enabling and/or enhancing the use of the reduced volume formulations of the invention. Jet nebulizers are particularly preferred, and one example is the PARI LC Plus® (Pari USA, Midlothian, Va., USA) nebulizer.

In one aspect, the modified amniotic fluid and/or amniotic fluid compositions can be used for treating or preventing a gastrointestinal disease or disorder. In some embodiments, the gastrointestinal disease or disorder is selected from the group consisting of intestinal atresia, irritable bowel syndrome (IBS), and constipation. In some embodiments, the modified amniotic fluid and/or amniotic fluid composition is administered to the site of gastrointestinal disease or disorder. The modified amniotic fluid and/or amniotic fluid composition can be delivered by any delivery method known by one of skill in the art, including, but not limited to, oral, buccal, intravenous, subcutaneous, intramuscular, by inhalation and the like. In some embodiments, the oral delivery method is a capsule. In further embodiments, the capsule has an enteric coating. In further embodiments, the enteric coating is a delayed-release coating. In some embodiments, the enteric coating is designed to release all or most of the modified amniotic fluid and/or amniotic fluid composition in the large intestine, and/or in the small intestine. In some embodiments, the modified amniotic fluid and/or amniotic fluid composition is administered in a weight-independent or weight-dependent dosage.

In an embodiment, the modified amniotic fluid and/or amniotic fluid composition is in the form of a powder. In an embodiment, the powder is a dry powder. The dry powder may be dried by any means known in the art, including conventional means (e.g. air drying, application of heat, including low heat) as well as lyophilization by freeze drying or spray drying.

In one aspect, the modified amniotic fluid and/or amniotic fluid compositions can be used for treating or preventing a wound. In one aspect, the modified amniotic fluid compositions can be applied to a wound, e.g., a wound resulting from an injury or a surgical procedure. The modified amniotic fluid components provide treatment to wound, such as facilitating wound healing, reducing or preventing inflammation and/or infection of the wound. The pharmaceutically acceptable carrier (e.g., by increasing the viscosity of the composition) retains or otherwise localizes the modified amniotic fluid and/or amniotic fluid composition, at the wound site for an extended period of time for sustained treatment of wound. In one aspect, the wound is a result of an injury. In one aspect, the wound is a result of a surgical procedure. In one aspect, the wound has an opening on the skin and the composition is administered to the site of the wound, for example, applied to the inside and/or the opening of the wound. In some embodiments, the modified amniotic fluid and/or amniotic fluid composition is administered in a weight-independent or area-dependent dosage.

In one aspect, the modified amniotic fluid compositions described herein are useful in enhancing or improving wound healing. The types of wounds that present themselves to physicians on a daily bases are diverse. Acute wounds are caused by surgical intervention, trauma and burns. Chronic wounds are wounds that are delayed in closing compared to healing in an otherwise healthy individual. Examples of chronic wound types plaguing patients include diabetic foot ulcers, venous leg ulcers, pressure ulcers, arterial ulcers, and surgical wounds that become infected.

The physician's goal when treating traumatic wounds is to heal the wound while allowing the patient to retain natural function in the area of the wound with minimal scaring and infection. If a wound becomes infected, it can lead to a loss of limb or life. For the most part, physicians heal these patients without incident. However, physicians dealing with chronic wounds are mainly concerned with closing the wound as quickly as possible to minimize the risk of an infection that could lead to loss of limb or life. Chronic wounds are wounds on patients that have comorbidities that complicate or delay the healing cascade. In one embodiment, the modified amniotic fluid compositions are administered to a patient with a chronic wound. In other embodiments, the modified amniotic fluid compositions are administered to a patient with an acute wound. In one aspect, the modified amniotic fluid compositions described herein can function as a tissue regeneration template that delivers essential wound healing factors, extracellular matrix proteins and inflammatory mediators to help reduce inflammation, enhance healing, and reduce scar tissue formation. In this aspect, the modified amniotic fluid compositions described herein are used in treating wounds amenable to negative pressure technology, including burns and ulcers, e.g., chronic ulcers, diabetic ulcers, decubitus ulcers and the like.

In another aspect, the modified amniotic fluid is used in conjunction with conventional treatments, including, but not limited to, negative pressure therapy, and may further be used in combination with matrices or scaffolds comprised of biocompatible materials, such as collagen, hyaluronic acid, gelatin or combinations thereof.

In another aspect, the modified amniotic fluid compositions described herein can be used to enhance wound healing and prevent scar formation as a result of a surgical incision. In one aspect, the modified amniotic fluid compositions can be applied to the open incision followed by suturing the incision. For example, the modified amniotic fluid compositions can be applied directly to the open incision by sprinkling the composition (e.g., in a lyophilized form) within the incision or by injecting the composition into the incision using a syringe, a small bellows device, or other related device. The modified amniotic fluid compositions are particularly useful where large incisions are produced by a surgical procedure. An example of such a procedure involves the treatment of spinal scoliosis, which requires a significant incision along the back of the subject. In one aspect, modified amniotic fluid compositions are useful in the healing of surgical incisions with minimal scarring. With respect to wound healing and the prevention of scar formation, the modified amniotic fluid compositions described herein can be used in combination with other wound healing products. For example, any of the placental tissue grafts or micronized placental tissue described herein can be applied to the wound before or after the modified amniotic fluid compositions have been applied. In some embodiments, the modified amniotic fluid and/or amniotic fluid composition is administered in a weight-independent or weight-dependent dosage.

In one aspect, the compositions described herein are useful in preventing or reducing scar formation on the spine or near the spine and sealing dural tears.

Depending upon the surgical procedure, the modified amniotic fluid compositions can be applied directly to the spinal dura, the surrounding region of the spine to include nerve roots, or a combination thereof. Due to the unique structure of vertebrae, the modified amniotic fluid compositions can be placed and affixed at the appropriate position in the subject. The modified amniotic fluid compositions can also provide proximal and distal barrier coverage where the spinal lamina has been removed for exposure to the affected area. In some embodiments, the modified amniotic fluid and/or amniotic fluid composition is administered in a weight-independent or weight-dependent dosage.

The modified amniotic fluid compositions are useful in preventing or reducing scar formation that can result from a variety of surgical procedures associated with the spine. The modified amniotic fluid compositions can be used after any procedure in the neck, mid-back, or lower back. The spinal dura is typically left unprotected following posterior procedures.

In other aspects, modified amniotic fluid compositions are useful for treating or preventing anterior procedures or modified anterior procedures such as Anterior Lumbar Interbody Fusion (ALIF) and Transforaminal Lumbar Interbody Fusion (TLIF). In these aspects, the modified amniotic fluid compositions provide additional protection to the vertebral surgical site by maintaining separation from the peritoneum, larger vessels, and abdominal musculature. The modified amniotic fluid compositions serves as a reduced friction anatomical barrier against adhesions and scaring. For example, the modified amniotic fluid compositions can prevent scar tissue from binding major blood vessels to the spine. This is a common problem with post-spinal surgery, and a second surgical procedure is required to address the problem. In some embodiments, the modified amniotic fluid and/or amniotic fluid composition is administered in a weight-independent or weight-dependent dosage.

The modified amniotic fluid compositions in combination with a pharmaceutically acceptable carrier, as taught herein, can be used as a patch to reduce the amount of scar tissue in the reproductive system after a surgical procedure. Scar tissue is another form of fibrous tissue and may also contribute to fertility problems. The ability to minimize the amount of scaring on the ovaries, or within the fallopian tubes may help with post-operative fertility and even pain. In another aspect, modified amniotic fluid compositions in combination with a pharmaceutically acceptable carrier can be used to reline the uterine wall after severe endometriosis treatments and increase the patient's ability to conceive. In a further aspect, modified amniotic fluid compositions can be used as an anti-adhesion barrier after removal of ovarian cyst or aid in the repair of vaginal wall erosion.

The modified amniotic fluid compositions in combination with a pharmaceutically acceptable carrier described herein can be used in general surgery procedures. For example, general surgical procedures include procedures related to the abdominal cavity. These include the intestines, stomach, colon, liver, gallbladder, appendix, bile ducts and thyroid glands. Procedures may include hernias, polypectomy, cancer removal, surgical treatment of Crohn's and ulcerative colitis. These procedures may be done open or laparoscopically. In other aspects, the modified amniotic fluid compositions in combination with a pharmaceutically acceptable carrier can be used to facilitate closure of anastomosis, an anti-adhesion barrier for anastomosis, or an anti-adhesion barrier for hernia repair.

In one aspect are disclosed methods for treating skin for cosmetic blemishes, the method comprising administering to a patient in need thereof an effective amount of a composition comprising amniotic fluid.

In some embodiments, the composition is applied to the skin after a cosmetic procedure. In one embodiment, the procedure is wrinkle reduction. In one embodiment, the procedure is scar reduction. In one embodiment, the procedure is pigmentation reduction. In one embodiment, the cosmetic procedure is laser skin resurfacing (lasabrasion, laser peel and laser vaporization), intense pulsed light, micro-needling (dermal needling), chemical peel, or microdermabrasion. In one embodiment, the composition is applied to skin after cosmetic surgery to reduce scarring. In some embodiments, the modified amniotic fluid and/or amniotic fluid composition is administered in a weight-independent or area-dependent dosage.

In one aspect, the amniotic fluid compositions can be used for treating or preventing a skin disease or disorder. In some embodiments, the skin disease or disorder is selected from the group consisting of hives, poison ivy, rash, blisters, hemorrhoids, cutaneous T-cell lymphoma, plaque psoriasis, atopic dermatitis, eczema, and dermatitis. In some embodiments, the composition is administered to the site of the skin disease or disorder. The amniotic fluid composition can be delivered by any delivery method known by one of skill in the art, including, but not limited to, topical, oral, buccal, intravenous, subcutaneous, intramuscular, by inhalation and the like. In preferred embodiments, the composition is delivered topically. In some embodiments, the modified amniotic fluid and/or amniotic fluid composition is administered in a weight-independent, weight-dependent, or area-dependent dosage.

In another aspect, the methods provided herein can be used in conjunction with conventional treatments.

In one aspect are disclosed methods for treating skin for cosmetic blemishes, the method comprising administering to a patient in need thereof an effective amount of a composition comprising amniotic fluid.

In some aspects, the compositions as described herein are administered via a mist (e.g., aerosolized, nebulized). In some embodiments, the mist is administered to the lungs by introduction to the air supply of an incubator (e.g., a premature baby incubator), or through the respiratory supply (e.g., ventilator, CPAP device, etc.). In some embodiments, the modified amniotic fluid and/or amniotic fluid composition is administered in a weight-independent or weight-dependent dosage.

In some aspects, the compositions are administered via a mist to a premature baby. A premature baby born before 37 weeks of gestation may have underdeveloped lungs. Administration of amniotic fluid directly to the lungs (e.g., as a mist) may aid in development of the lungs. Preferably, the amniotic fluid is from a near-term donor, it is contemplated that the amniotic fluid from near-term donors will provide natural regulators of normal fetal lung development. In some embodiments, the modified amniotic fluid and/or amniotic fluid composition is administered in a weight-independent or weight-dependent dosage.

Dosages

In some embodiments, the modified amniotic fluid and/or composition may be administered by continuous infusion. In embodiments, the administration may continue for periods of from 1 minute to 1 week or longer. In other embodiments, the modified amniotic fluid and/or composition may be administered by doses at intervals of, e.g., every 1, 2, 4, 6, 8, or 12 hour(s), daily, every other day, three times per week, or one time each week, two weeks, three weeks, monthly, bimonthly, etc.

Weight-Independent Dosages

In some embodiments, the modified amniotic fluid and/or composition is administered to the subject at a dose of between about 0.01 µg and about 10,000 mg, including but not limited to about 0.01 µg, 0.5 µg, 1 µg, 5 µg, 10 µg, 100 µg, 250 µg, 500 µg, 1 mg, 3 mg, 5 mg, 10 mg, 50 mg, 100 mg, 250 mg, 500 mg, 1000 mg, and 2000 mg. In some embodiments, the modified amniotic fluid and/or composition is administered to the subject at a dose range of between about 0.01 µg-2000 mg, 0.5 µg-1000 mg, 1 µg-500 mg, 5 µg-250 mg, 10 µg-100 mg, 100 µg-50 mg, 250 µg-10 mg, 500 µg-5 mg, 1 mg-3 mg, 0.5 mg to 100 mg, and 1 mg to 50 mg. In some instances, the dose can be even higher. The present invention encompasses every sub-range within the cited ranges and amounts.

In some embodiments, the modified amniotic fluid and/or composition is administered to the subject at a dose of between about 0.1 µl and about 10,000 ml, including but not limited to about 0.1 µl, 5 µl, 10 µl, 100 µl, 250 µl, 500 µl, 1 ml, 3 ml, 5 ml, 10 ml, 50 ml, 100 ml, 250 ml, 500 ml, 1000 ml, and 2000 ml. In some embodiments, the modified amniotic fluid and/or composition is administered to the subject at a dose range of between about 0.1 µl-2000 ml, 5 µl-1000 ml, 10 µl-500 ml, 50 µl-250 ml, 100 µl-100 ml, 500 µl-50 ml, 1 ml-10 ml, and 3 ml 5 ml. In some instances, the dose can be even higher. The present invention encompasses every sub-range within the cited ranges and amounts.

Weight-Dependent Dosages

In some embodiments, the modified amniotic fluid and/or composition is administered to the subject at a dose of between about 0.001 µg/kg and about 1000 mg/kg, including but not limited to about 0.001 µg/kg, 0.01 µg/kg, 0.05 µg/kg, 0.1 µg/kg, 0.5 µg/kg, 1 µg/kg, 10 µg/kg, 25 µg/kg, 50 µg/kg, 100 µg/kg, 250 µg/kg, 500 µg/kg, 1 mg/kg, 2.5 mg/kg, 5 mg/kg, 10 mg/kg, 25 mg/kg, 50 mg/kg, 100 mg/kg, and 200 mg/kg. In some embodiments, the modified amniotic fluid and/or composition is administered to the subject at a dose range of between about 0.01 µg/kg-200 mg/kg, 0.05 µg/kg-100 mg/kg, 0.1 µg/kg-50 mg/kg, 0.5 µg/kg-25 mg/kg, 1 µg/kg-10 mg/kg, 10 µg/kg-5 mg/kg, 25 µg/kg-1 mg/kg, 50 µg/kg-500 µg/kg, 100 µg/kg-250 µg/kg, and 10 µg/kg to 2.5 mg/kg. In some instances, the dose can be even higher, e.g., as high as 2,000, 5,000, 10,000, or 50,000 mg/kg or higher. The present invention encompasses every sub-range within the cited ranges and amounts.

In some embodiments, the modified amniotic fluid and/or composition is administered to the subject at a dose of between about 0.001 µl/kg and about 1000 ml/kg, including but not limited to about 0.001 µl/kg, 0.01 µl/kg, 0.05 µl/kg, 0.1 µl/kg, 0.5 µl/kg, 1 µl/kg, 10 µl/kg, 25 µl/kg, 50 µl/kg, 100 µl/kg, 250 µl/kg, 500 µl/kg, 1 ml/kg, 5 ml/kg, 10 ml/kg, 25 ml/kg, 50 ml/kg, 100 ml/kg, and 200 ml/kg. In some embodiments, the modified amniotic fluid and/or composition is administered to the subject at a dose range of between about 0.01 µl/kg-200 ml/kg, 0.05 µl/kg-100 ml/kg, 0.1 µl/kg-50 ml/kg, 0.5 µl/kg-25 ml/kg, 1 µl/kg-10 ml/kg, 10 µl/kg-5 ml/kg, 25 µl/kg-1 ml/kg, 50 µl/kg-500 µl/kg, and 100 µl/kg-250 µl/kg. In some instances, the dose can be even higher, e.g., as high as 2,000, 5,000, 10,000, or 50,000 ml/kg or higher. The present invention encompasses every sub-range within the cited ranges and amounts.

Area-Dependent Dosages

In one embodiment, the modified amniotic fluid and/or composition is administered at a dose of about 0.2 to about 100.0 mg/m$^2$, e.g., about 0.6 to about 40.0 mg/m$^2$, about 1.0 to about 30.0 mg/m$^2$, or about 2.0 to about 20 mg/m$^2$. In some instances, the dose can be even lower, e.g., as low as 0.1, 0.05. 0.01. 0.005, or 0.001 mg/m$^2$ or lower. In some instances, the dose can be even higher, e.g., as high as 200, 500, or 1000 mg/m$^2$ or higher. The present invention encompasses every sub-range within the cited ranges and amounts.

In one embodiment, the modified amniotic fluid and/or composition is administered at a dose of about 0.2 to about 100.0 ml/m$^2$, e.g., about 0.6 to about 40.0 ml/m$^2$, about 1.0 to about 30.0 ml/m$^2$, or about 2.0 to about 20 mg/m$^2$. In some instances, the dose can be even lower, e.g., as low as 0.1, 0.05. 0.01. 0.005, or 0.001 ml/m$^2$ or lower. In some instances, the dose can be even higher, e.g., as high as 200, 500, or 1000 ml/m$^2$ or higher. The present invention encompasses every sub-range within the cited ranges and amounts.

The effective dosage will depend on many factors including the gender, age, weight, and general physical condition of the subject, the severity of the condition warranting treatment, the particular compound or composition being administered, the duration of the treatment, the nature of any concurrent treatment, the route of administration, the carrier used, and like factors within the knowledge and expertise of those skilled in the art. As appropriate, a treatment effective amount in any individual case can be determined by one of ordinary skill in the art by reference to the pertinent texts and literature and/or by using routine experimentation (see, e.g., Remington, *The Science and Practice of Pharmacy* (21$^{st}$ ed. 2005), which is hereby incorporated by reference in its entirety).

Apparatuses and Methods for Application

As described above, in some methods of administration, the composition is applied as a coating, a patch, or a bandage or injected onto or into a location of treatment. The composition may also be sprayed or brushed onto a location of treatment.

Figure 3:
Figure 4:
Figure 5:
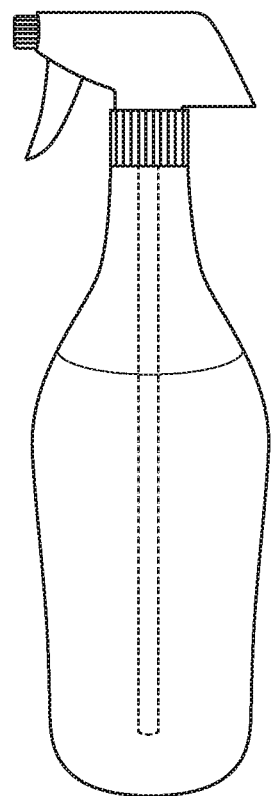
Figure 6:
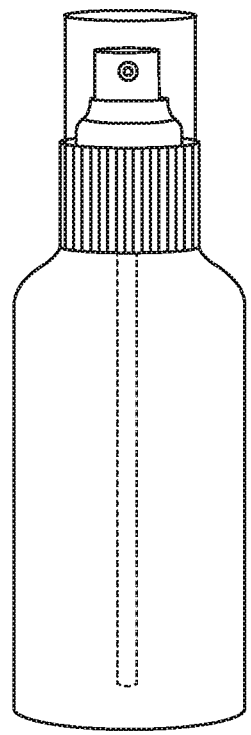
Figure 7:
Figure 8:
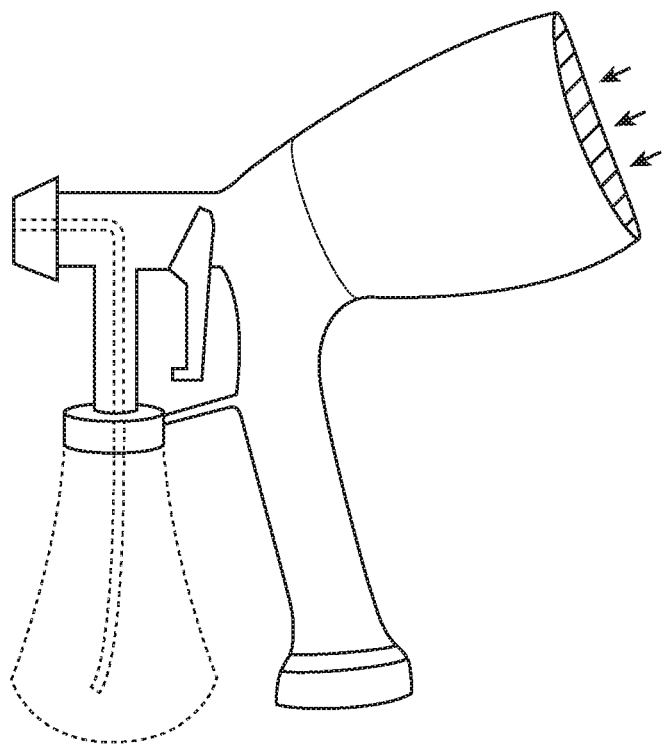

In some embodiments, each of the modified amniotic fluid and pharmaceutically acceptable carrier are in liquid form. Each may be stored separately and applied sequentially. For example, each of the modified amniotic fluid and pharmaceutically acceptable carrier compositions may be stored in separate bottles or other containers, such as, for example, any of the containers shown in FIGS. 1-9. Each of the containers shown in FIGS. 1-9 are known to those skilled in the art of containers. The administration apparatus may be, for example, a squeeze bottle with a narrowed spout for controlled extrusion and delivery of a gel or liquid contained therein, such as in FIG. 1. Alternatively, the administration apparatus may be a container with an applicator stored on an interior portion of the cap, such as in FIG. 2. In such embodiments, the applicator may be, for example, a brush with bristles or a sponge. The applicator may be disposed at the end of a stick or other extension so as to extend significantly into the interior of the container when the cap is secured onto the container. In other embodiments, the administration apparatus may be a bottle with an applicator tip extending from a proximal end of the apparatus, wherein a proximal end is the end that is applied to the patient subject. The applicator tip may be, for example, a rolling ball or a sponge, as shown in FIGS. 3 and 4, respectively. Such bottles may be squeezable. Alternatively, the bottle may be substantially rigid and the liquid applied via gravity when the applicator is positioned below the remainder of the bottle. In other embodiments, the container may include a syringe, which is depressible, such as shown in FIG. 7. In such embodiments, pressure is created inside the container when the syringe is depressed, which causes liquid or gel inside the container to be extruded from the proximal tip of the container nozzle.

Figure 9:
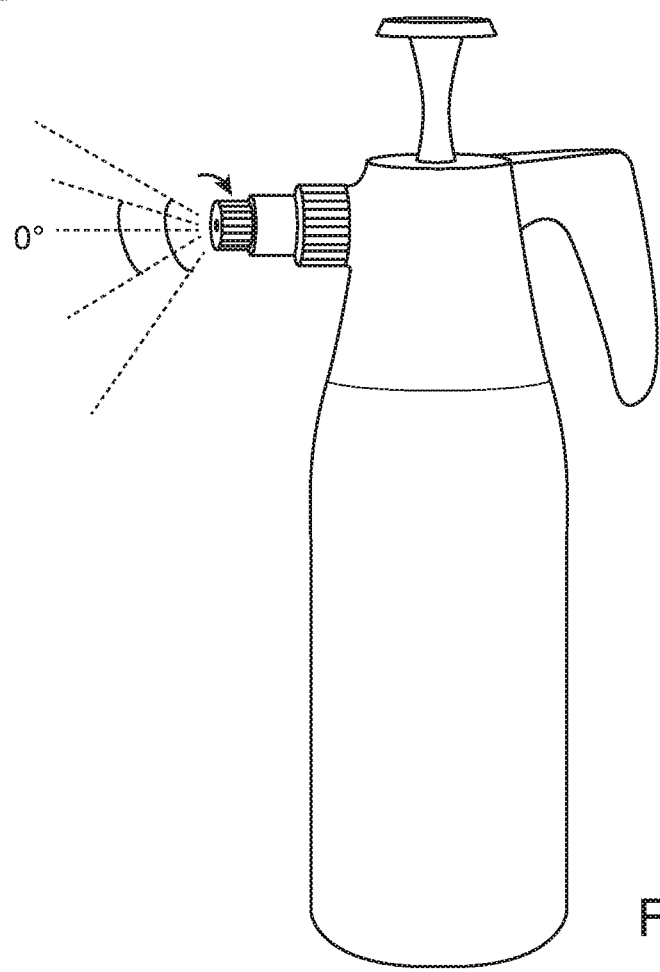

In still other embodiments, one or more of the modified amniotic fluid and/or amniotic fluid and pharmaceutically acceptable carrier compositions may be administered to a subject via a spray bottle. Various spray bottles are known, and any suitable spray bottle technology may be employed here. For example, atomizing sprayers, such as those depicted in FIGS. 5 and 6, may be used. With atomizing sprayers, a nozzle may be pulled or a top depressed, which causes compression of a spring within a straw or movement of other object within the container, thereby causing pressure within the straw to drop. The pressure drop causes liquid from the container to enter the straw and projects it forward at a speed that causes it to eject from the container as a mist of fine droplets. Similarly, high volume low pressure (HVLP) sprayers or pump sprayers, such as those shown in FIGS. 8 and 9, respectively, may be used. Such sprayers create pressure within the container, either through the uptake of air (HVLP sprayer of FIG. 8) or through the depression of a pump (pump sprayer of FIG. 9), which causes the liquid to escape the container through the nozzle. In various spraying embodiments, a fan tip nozzle may be used to control the angle of the spray. For example, as shown in FIG. 9, in some embodiments, the nozzle may be turned to achieve various spray angles ranging from approximately 0 degrees to approximately 120 degrees or more.

In other embodiments, as described above in the previous section, a combination formulation may be created, which comprises a liquid or gel-like formulation formed of both modified amniotic fluid and/or amniotic fluid and a pharmaceutically acceptable carrier. In embodiments containing both the modified amniotic fluid and/or amniotic fluid and pharmaceutically acceptable carrier in a single combination, any suitable application apparatus, such as any of the apparatuses described above and depicted in FIGS. 1-9 may be used to apply the formulation to a subject.

As described above, in preferred embodiments, simultaneous application of the modified amniotic fluid and/or amniotic fluid and pharmaceutically acceptable carrier compositions is desired; however, some embodiments of the two compositions are reactive and must be stored separately. In such embodiments, a dual delivery device may be used. Non-limiting examples of dual delivery devices are depicted in FIGS. 10-13.

Figure 10:
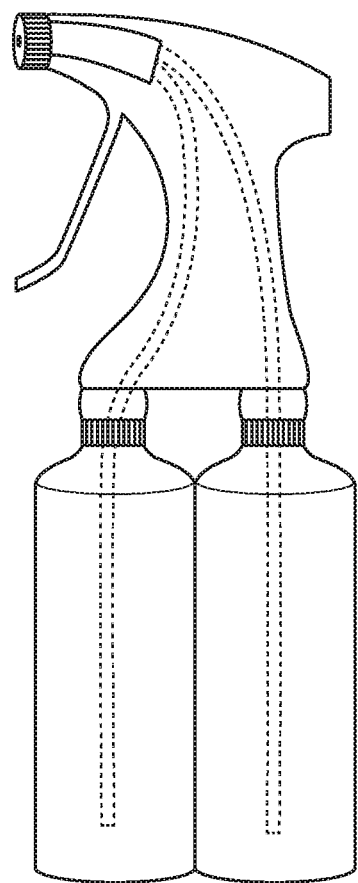
Figure 11:
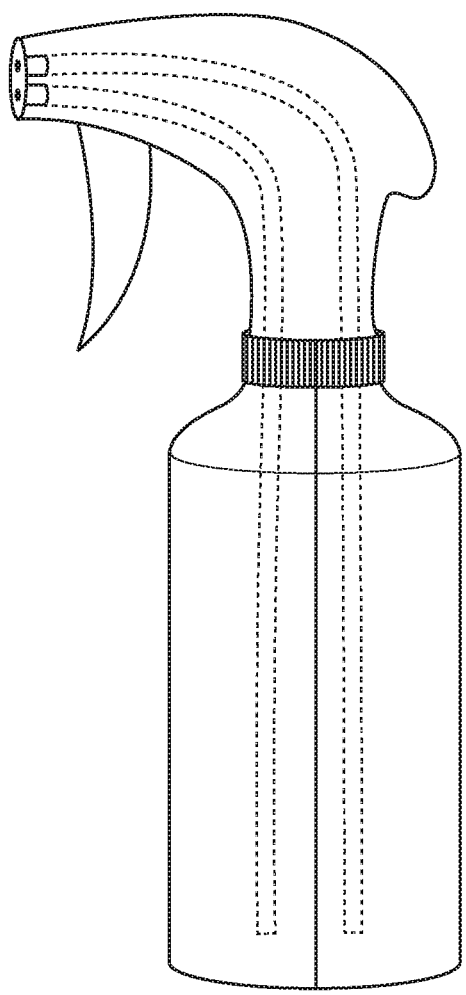

In particular, FIGS. 10-11 depict two examples of dual chamber atomizing sprayers. As shown, a top/head portion of the sprayer, which includes the nozzle, is connected to two chambers. A modified amniotic fluid composition, such as any embodiment of a liquid modified amniotic fluid composition described above, is provided within a first chamber. Alternatively, an amniotic fluid composition, such as any embodiment of a liquid amniotic fluid composition described above, is provided within a first chamber. A pharmaceutically acceptable carrier, such as any embodiment of a pharmaceutically acceptable carrier described above, is provided within a second chamber. In some embodiments, each chamber is a separate bottle, for example, as shown in FIG. 10. In other embodiments, two separate, liquid-tight chambers are provided within the same bottle, for example, as shown in FIG. 11. In FIG. 11, the chambers are side by side. In other embodiments, a first chamber may be disposed within, and surrounded by, a second chamber.

In various embodiments, a first straw extends from the top/head portion into the first chamber and a second straw extends from the top/head portion into the second chamber. Each straw may include a springe, which compresses when a handle of the sprayer is pulled, causing the pressure to drop within both straws, and causing uptake of liquid into both straws. As shown in FIG. 10, in some embodiments, one end of each straw terminates at or in a mixing reservoir disposed within the top/head portion of the sprayer. In such embodiments, the modified amniotic fluid and/or amniotic fluid composition and the pharmaceutically acceptable carrier come into contact and mix briefly within the mixing reservoir before being ejected from a single, shared nozzle as an aerosolized spray. As shown in FIG. 11, in other embodiments, it may be advantageous to avoid any mixing of the components prior to ejection from the sprayer. In such embodiments, the sprayer may be provided with two nozzles. A first nozzle may be in fluid communication with the first chamber, and a second nozzle may be in fluid communication with the second chamber. For example, in some embodiments, the first nozzle connects to a first reservoir, which connects to the first straw; in other embodiments, the first straw connects directly to the first nozzle. Similarly, the second nozzle may connect to a second reservoir, which connects to the second straw, or the second straw may connect directly to the second nozzle. In embodiments having two nozzles, the nozzles are preferably positioned close together such that the droplets of the modified amniotic fluid and/or amniotic fluid and the droplets of the pharmaceutically acceptable carrier mix as they are ejected from the sprayer.

Figure 12:
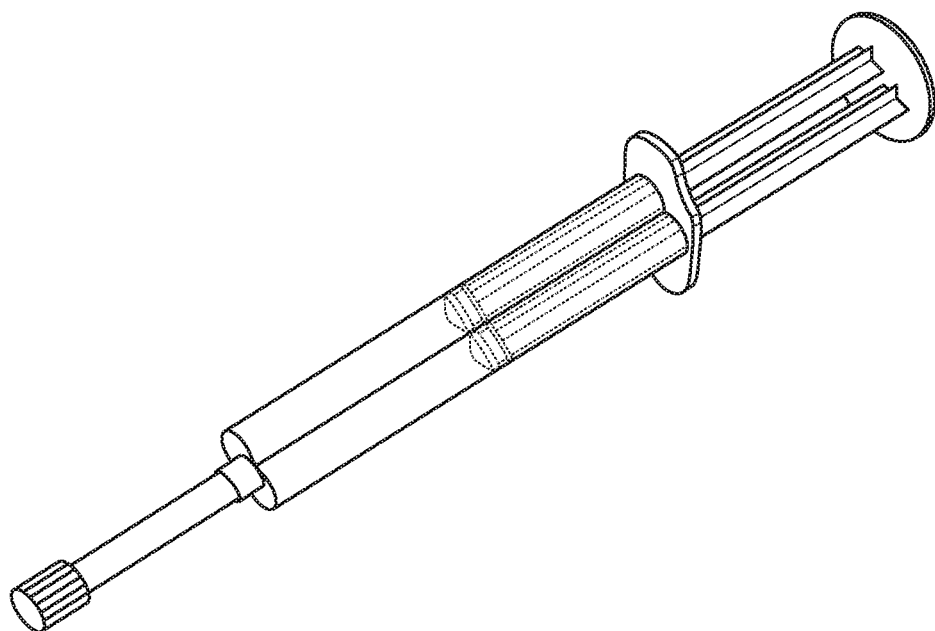
Figure 13:
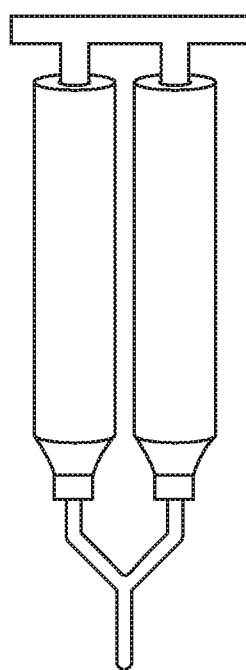

FIGS. 12-13 depict examples of a double syringe, which may be used to simultaneously administer a micronized placental tissue composition and an adhesive or gelation agent composition to a subject. A first chamber or vial of the syringe is provided with the micronized placental tissue composition and a second chamber is provided with the adhesive or gelation agent composition (or vice versa). The first chamber is connected to a first delivery tube or needle and a second chamber is connected to a second delivery tube or needle. An aperture is disposed at a proximal tip of each delivery tube or needle.

In at least some embodiments, the two chambers are disposed side by side, and the two delivery tubes or needles are disposed side by side. Each chamber is provided with a plunger. When depressed, each plunger moves proximally, decreasing the volume of each chamber, and thereby causing the contents of each chamber to be expelled through the delivery tube or needle and out the proximal aperture. In such embodiments, the two plungers are connected, for example, via a shared top surface, to facilitate simultaneous and equal movement of the plungers. Such a feature may help ensure equal application of the micronized placental tissue composition and the adhesive or gelation agent composition. In some embodiments, an equal ratio may not be desired. In such embodiments, the size of the chambers and/or the diameter of the delivery tubes or needles may vary so that a desired ratio of micronized placental tissue composition to adhesive or gelation agent composition is expelled from the syringe upon depression of the plungers.

Optionally, in some embodiments of a double syringe, an applicator is connected to a proximal end of the delivery tubes or needles to facilitate application and/or mixing of the liquid compositions. For example, in some embodiments, a brush or scraper is disposed at the proximal end (see FIG. 12). In such embodiments, depressing the syringe causes the modified amniotic fluid and the pharmaceutically acceptable carrier to be expelled onto the applicator. The applicator can then be brushed or gentle scraped against the subject to apply and combine the two compositions. In other embodiments, the applicator is a connector, which is attached at its distal end to the proximal ends of both the first and second delivery tubes or needles, and which defines a single lumen at its proximal end (see FIG. 13). In such embodiments, mixing of the compositions may occur within the connector before being expelled from the proximal end of the single lumen.

EXAMPLES

The following examples are intended to further illustrate certain embodiments of the disclosure. The examples are put forth so as to provide one of ordinary skill in the art with further illustration of the invention and are intended to be purely exemplary, and are not intended to limit its scope.

Example 1

The amniotic fluid first undergoes a two-step dialysis process. First, the amniotic fluid is passed through a 3 kiloDalton (kDa) filter to remove low molecular weight urea and uric acid, in addition to reducing the water content. Second, the amniotic fluid is again passed through a 3 kDa membrane in the presence of a dialysate solution (normal saline), to flush the remainder of the urea and uric acid, while maintaining the volume of the fluid. Cryopreservative is added such that the final product contains equal volumes dialyzed fluid and cryopreservative; therefore, the finished product is approximately 1.5 times more concentrated than the starting fluid. The product is then aliquoted into vials (using aseptic technique) and frozen.

It is contemplated that this removal will not have an impact on the components of the AF thought to confer benefit, such as the hyaluronic acid and other proteins in the fluid.

Example 2

The amniotic fluid may optionally be lyophilized. When the fluid is lyophilized, this is preferably done after the two-step dialysis but without addition of cryopreservative.

After the second dialysis, the resulting fluid is frozen at −80° C. The fluid is then dried under vacuum. Lyophilized amniotic fluid can be stored at room temperature.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

In addition, where the features or aspects of the invention are described in terms of Markush groups, those skilled in the art will recognize that the invention is also thereby described in terms of any individual member or subgroup members of the Markush group.

All publications, patent applications, patents and other references mentioned herein are expressly incorporated by reference in their entirety, to the same extent as if each were incorporated by reference individually. In case of conflict, the present specification, including definitions, will control.

What is claimed is:

1. A composition comprising an amount of modified amniotic fluid wherein said amniotic fluid is sterilized and desalted;
   wherein the modified amniotic fluid has been desalted to remove all or substantially all salts; or
   wherein the modified amniotic fluid has a salt concentration of 0.9% saline +/−0.1%.

2. The composition of claim 1, wherein the modified amniotic fluid is free or substantially free of material greater than 1 µm in size.

3. The composition of claim 1, wherein the modified amniotic fluid is human amniotic fluid.

4. The composition of claim 1, wherein the modified amniotic fluid is free or substantially free of cells and/or cellular debris.

5. The composition of claim 1, further comprising a pharmaceutically acceptable carrier.

6. The composition of claim 5, wherein the modified amniotic fluid and pharmaceutically acceptable carrier have a weight ratio in the range between 1:10 and 10:1.

7. The composition of claim 5, wherein the pharmaceutically acceptable carrier is Wharton's jelly, a biocompatible gelation agent, a polysaccharide, hyaluronic acid, poly-1-lysine, or collagen.

8. The composition of claim 1, wherein the composition is injectable; is a topical composition; or is a liquid, gel, or paste.

9. The composition of claim 1, wherein the composition is a sprayable composition.

10. A solid pellet comprising a dried droplet of the composition of claim 1.

11. A molded composition comprising an amount of the composition of claim 1 dried in a mold.

12. A composition comprising an amount of the composition of claim 1 and a placental tissue graft.

13. A composition comprising an amount of the composition of claim 1 and an amount of micronized placental tissue particles.

14. A method for treating a gastrointestinal disease or disorder, a skin disease or disorder, a pulmonary disease or disorder, the method comprising administering to a patient in need thereof an amount of a composition comprising an amount of modified amniotic fluid wherein said amniotic fluid is sterilized and desalted;

wherein the modified amniotic fluid has been desalted to remove all or substantially all salts; or wherein the modified amniotic fluid has a salt concentration of 0.9% saline +/−0.1%.

15. A method for treating a patient who has undergone a cosmetic procedure, the method comprising administering to the patient an effective amount of a composition comprising an amount of modified amniotic fluid wherein said amniotic fluid is sterilized and desalted;

wherein the modified amniotic fluid has been desalted to remove all or substantially all salts; or wherein the modified amniotic fluid has a salt concentration of 0.9% saline +/−0.1%.

16. A method for preventing or reducing scar formation on the spine or near the spine, or sealing a dural tear, or for treating or preventing an anterior procedure or a modified anterior procedure, the method comprising administering to a patient in need thereof an effective amount of a composition comprising an amount of modified amniotic fluid wherein said amniotic fluid is sterilized and desalted;

wherein the modified amniotic fluid has been desalted to remove all or substantially all salts; or wherein the modified amniotic fluid has a salt concentration of 0.9% saline +/−0.1%.

17. A method for enhancing wound healing or preventing scar formation as a result of a surgical incision, or for reducing the amount of scar tissue in a reproductive system after a surgical procedure, the method comprising administering to a patient in need thereof an effective amount of a composition comprising an amount of modified amniotic fluid wherein said amniotic fluid is sterilized and desalted;

wherein the modified amniotic fluid has been desalted to remove all or substantially all salts; or wherein the modified amniotic fluid has a salt concentration of 0.9% saline +/−0.1%.

18. The composition of claim 1, wherein the modified amniotic fluid has been desalted to remove all or substantially all salts.

19. The composition of claim 1, wherein the modified amniotic fluid has a salt concentration of 0.9% saline +/−0.1%.

\* \* \* \* \*